US010799384B2

(12) United States Patent
Callow (10) Patent No.: US 10,799,384 B2
(45) Date of Patent: Oct. 13, 2020

(54) SEXUAL AID DEVICE, SYSTEM AND ENCORE METHOD OF INTERCOURSE

(71) Applicant: Stephen A. Callow, Fort Lauderdale, FL (US)

(72) Inventor: Stephen A. Callow, Fort Lauderdale, FL (US)

(73) Assignee: Perfect Fit Brand, Inc., Fort Lauderdale, FL (US)

( * ) Notice: Subject to any disclaimer, the term of this patent is extended or adjusted under 35 U.S.C. 154(b) by 238 days.

(21) Appl. No.: 15/913,901

(22) Filed: Mar. 6, 2018

(65) Prior Publication Data

US 2019/0274868 A1    Sep. 12, 2019

(51) Int. Cl.
*A61F 5/41* (2006.01)

(52) U.S. Cl.
CPC .......... *A61F 5/41* (2013.01); *A61F 2005/411* (2013.01); *A61F 2005/414* (2013.01)

(58) Field of Classification Search
CPC ......... A61F 5/41; A61F 2005/411; A61F 6/04
USPC ..................................................... 600/38–41
See application file for complete search history.

(56) References Cited

U.S. PATENT DOCUMENTS

| 844,798 | A | * | 2/1907 | Hawley | A61F 5/41 600/39 |
| 3,759,254 | A | * | 9/1973 | Clark | A61F 6/04 600/39 |
| 4,429,689 | A | * | 2/1984 | Yanong | A61F 5/41 600/39 |
| 6,436,031 | B1 | * | 8/2002 | Salib | A61F 5/41 600/39 |

* cited by examiner

*Primary Examiner* — Samuel G Gilbert
(74) *Attorney, Agent, or Firm* — Peter A. Koziol; Assouline & Berlowe, PA (57) ABSTRACT

A sexual aid device, system and method that provide a chassis with a distal end; a proximal end with at least one penile port; at least one penile support between the distal end and proximal end; at least one penile channel between the distal end and proximal end; wherein the chassis is configured to have an opening along the top toward the proximal end and an upper chassis plate is securable in a closed position. When used with a sleeve and chassis cover the system provides additional support so that the combined device substantially surrounds the donning penis and enables new methods of intimate sexual intercourse without an erection and without substantially obstructing blood flow to and from the penis. In an optional saddled embodiment the inner and outer scrotal support of the chassis and sheath help to hold the device in place while providing a comfortable scrotal opening an enabling gentle massage of the scrotum and perineum through use of a perineum bump.

17 Claims, 11 Drawing Sheets

FIG. 16

SEXUAL AID DEVICE, SYSTEM AND ENCORE METHOD OF INTERCOURSE

CROSS-REFERENCE TO RELATED APPLICATIONS

This invention improves upon prior inventions of the inventor See, e.g., Stephen Callow, Unified Dildo and Bottom Open Anatomically Contoured Harness Plate, U.S. Appl. Pub. No. US20160279019A1 filed Mar. 26, 2015; Stephen Callow, Personal cleaning device U.S. Appl. Pub. No. US20090082729A1, filed Sep. 26, 2007; Stephen Callow, Hollow Plug, U.S. Pat. No. D742,025, issued Oct. 27, 2015; and Stephen Callow, Hollow dildo, U.S. Pat. No. D719,665 issued Dec. 16, 2014, each of which are incorporated herein by reference in their entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The invention relates to the fields of sexual health devices, systems and methods for sexual intercourse. The invention provides a solution for erectile dysfunction. The invention enables sexual intercourse with a flaccid penis and also enables sexual intercourse to begin or continue after climax.

Description of the Related Art

Erectile dysfunction is treated in a variety of manners. Common treatments include drugs such as: Avanafil (Stendra); Sildenafil (Viagra); Tadalafil (Adcirca, Cialis); Vardenafil (Levitra, Staxyn). Generally, these drugs enhance the effects of nitric oxide and natural chemicals in the body that relax muscles in the penis and/or increase blood flow in the penis. Generally, taking one of these drugs will not automatically produce an erection, but enables the user to form an erection once the drug is active and nitric oxide is released.

Other drugs such as alprstadil can be administered through self-injection. With this method the user or their partner injects alprostadil (caverject impuls, edex, etc.) into the base or side of the penis. Other drugs such as paverine and pentolamine might also be used alone or in conjunction with (bimix/trimix) with alprostadil. In some cases, these drugs may cause more immediate erections than oral medications. However, there can be pain and bleeding at the injection site, formation of fibrous tissue, nerve damage, infection and in some cases prolonged erection (priapism). Alternative methods of application of the drugs include urethral suppositories. These suppositories and the tools that insert them can be painful and the overall treatment suffers from many of the same problems as with other drugs.

Other possible side effects of treating ED with drugs include flushing, nasal congestion, headache, visual changes, backache and stomach upset In some cases allergic reactions, sever pain, death and suicide may result. Medications for erectile dysfunction do not work in all men and might be less effective in certain conditions, such as after prostate surgery or if the persons afflicted have diabetes. Some medications might also be dangerous if the afflicted persons: take nitrate drugs such as: isosorbide mononitrate (Monoket) and isosorbide dinitrate Dilatrate-SR, Isordil), nitroglycerin (Minitran, Nitro-Dur, Nitrostat, etc.) and others. Drugs may also be dangerous for those that have heart disease, heart failure and low blood pressure (hypotension). In addition or in lieu of drugs, afflicted persons may be treated with hormones such as testosterone replacement. This can have many of the same side effects as drugs and also cause other changes in the body and mood of the user.

Instead of and/or to supplement drugs and hormones, afflicted persons may use herbal supplements and alternative medicine. Some of these can be dangerous and may have unknown methods of work and may interact with prescription drugs or be contaminated during formulation.

Generally, change of lifestyle and exercise has shown to improve erectile function in some men, such as quitting smoking, abstaining from alcohol and recreational drug use, losing excess pounds, reducing stress and psychological therapy. Such treatments take time and discipline and might not always be effective or appropriate.

In lieu or in addition to other therapies, surgery and penile implants are sometimes a solution. This form of treatment typically involves surgically placing devices into the penis. The devices may include inflatable or bendable rods. The inflatable devices enable the user some control how long they have an erection whereas the bendable rods help the penis be firm and malleable. Surgery is risky, generally permanent and can have many side effects, injuries and drawbacks including but not limited to permanent pain, greater dysfunction and or infection.

Yet, another alternative is the use of vacuum construction devices (also known as penis pumps or "VCD"), and erectile rings. Generally, such devices are used by placing a tube over the afflicted penis. Then the pump removes air from inside the tube. This creates a vacuum that pulls blood into the penis causing an erection. A tension ring is then placed around the base of the penis to restrict the blood from leaving and keep the penis firm. The penis pump may damage or bruise the penis is a possible and ejaculation is often restricted by the tension ring. The use of a VCD can also result in a colder feeling penis than one that has become erect naturally. The inventor has created many devices that can be helpful for extended sexual intercourse and use by those that suffer from erectile dysfunction or premature ejaculation. However, these inventions do not provide the unique benefits for better fit, form, method of use and manufacture, particularly when used with a flaccid penis.

However, there is a long unmet need for a device that does not rely upon drugs or restricting blood flow from the penis that can be used on the fly that is comfortable and erotic for use and that promotes sexual wellness. Moreover, although the inventor has created many devices that can be helpful for extended sexual intercourse and use by those that suffer from erectile dysfunction or premature ejaculation. See, e.g., Stephen Callow, Unified Dildo and Bottom Open Anatomically Contoured Harness Plate, U.S. Appl. Pub. No. US20160279019A1 filed Mar. 26, 2015; Stephen Callow, Personal cleaning device U.S. Appl. Pub. No. US20090082729A1, filed Sep. 26, 2007; Stephen Callow, Hollow Plug, U.S. Pat. No. D742,025, issued Oct. 27, 2015; and Stephen Callow, Hollow dildo, U.S. Pat. No. D719,665 issued Dec. 16, 2014, each incorporated herein by reference in their entirety. However, none of those inventions provide the unique structure disclosed herein that fills long felt needs for better fit, form, new methods of use and superior manufacture, particularly when used with a flaccid penis.

SUMMARY OF THE INVENTION

The present invention is a sexual aid device, system and encore method of intercourse.

More specifically, the sexual aid device, system and encore method of intercourse enables intercourse for person with a flaccid penis due to erectile dysfunction, sexual exhaustion (post climax). It also provides enhanced sexual experience persons with normal and above normal sexual drive and ability.

With the invention of the sexual aid device, system and encore method of intercourse. disclosed herein now sexual partners can try previously avoided positions with new confidence, comfort and pleasure. The invention enables deeper penetration for longer times, and is easy to don by a user with a flaccid or exhausted penis.

Although the invention is illustrated and described herein as embodied as a sexual aid device, system and encore method of intercourse, the invention is not limited to the details shown because various modifications and structural changes may be made without departing from the invention and the equivalents of the claims. However, the construction and method of operation of the invention together with additional objects and advantages thereof will be best understood from the following description of specific embodiments when read in connection with the accompanying drawings.

BRIEF DESCRIPTION OF THE DRAWINGS

Features and advantages of the present invention will become apparent to those skilled in the art from the following description with reference to the drawings, in which.

DETAILED DESCRIPTION OF THE INVENTION

Figure 1:
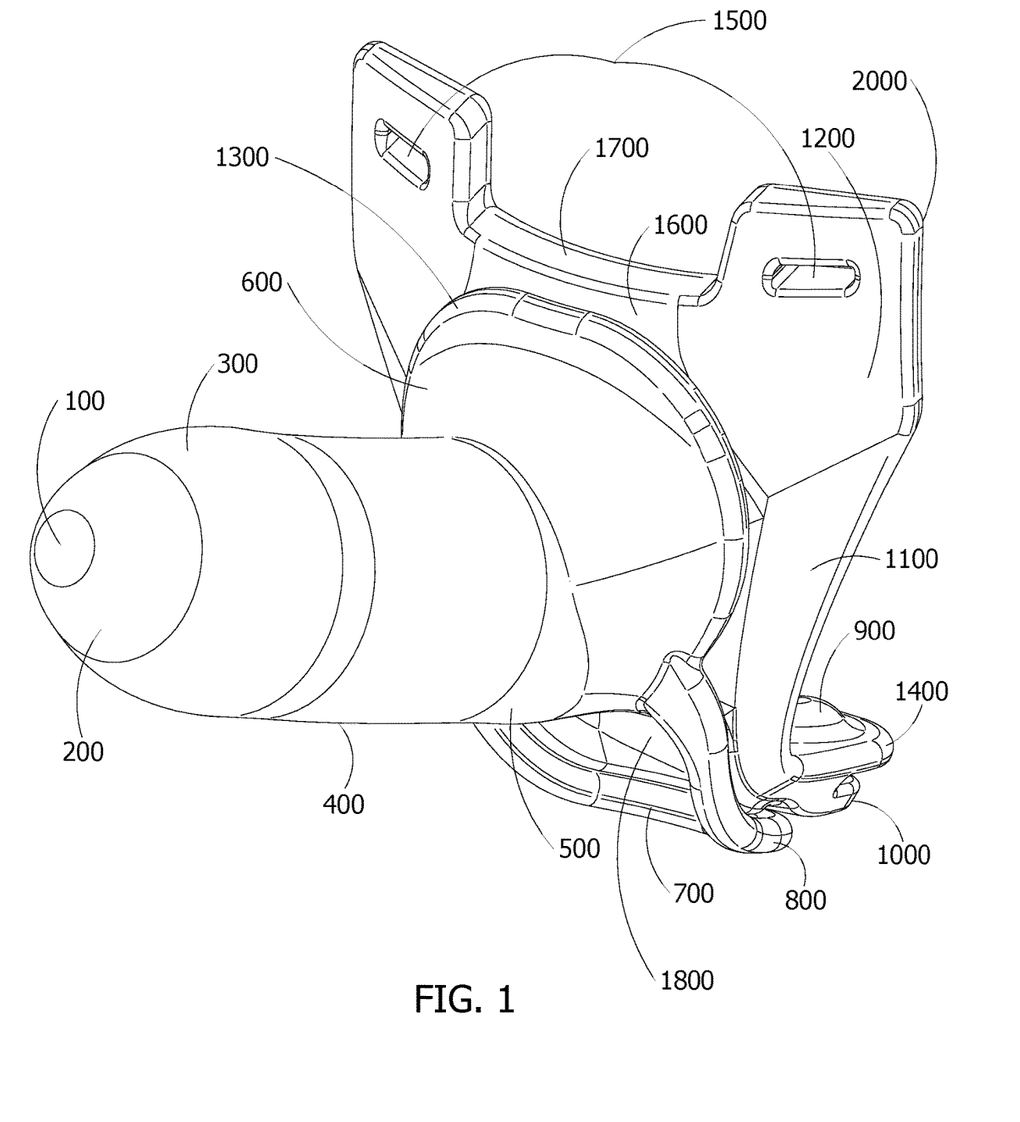
FIG. 1 is an elevated distal view of the assembled sexual aid device and system of the present invention.
Figure 3:
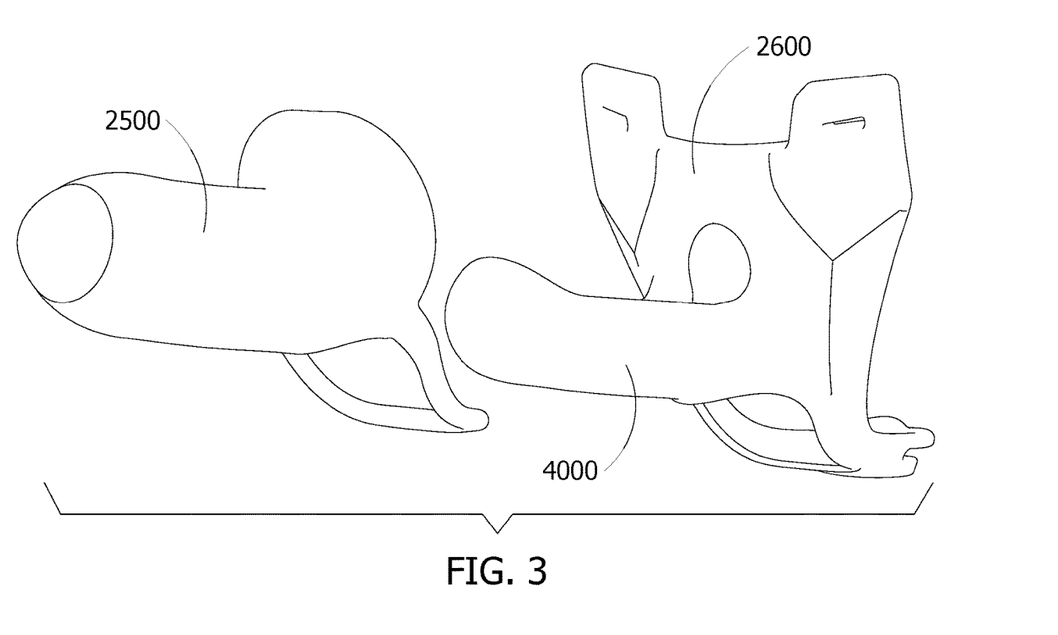
FIG. 3 is an exploded distal view of the invention shown in FIG. 1.

Referring to the drawings, FIG. 1. shows an elevated distal view of an embodiment of the assembled sexual aid device and system of the present invention, which as drawn in FIG. 3 comprises a sheath 2500 and a chassis 2600. As drawn in FIG. 1, in one embodiment the sheath comprises a sheath outer distal center tip 100, a sheath outer distal outer tip 200, a sheath outer distal shaft 300, sheath outer center shaft 400, a sheath outer proximal shaft 500, a sheath outer flange 600, a sheath inner scrotal support 700, a sheath outer scrotal support 800. The sheath inner scrotal support 700 and sheath outer scrotal support 800 surround the scrotal opening 1800 and form the saddle of the sheath. The sheath 2500 and chassis 2600 have proximal and distal ends relative to the donning user.

As further drawn in the embodiment disclosed in FIG. 1, the chassis comprises a perineum bump 900, outer perineum notch 1000, harness plate distal side section 1100, harness plate distal upper region 1200, outer ridge of the sheath flange 1300, inner perineum notch 1400, harness plate strap slots 1500, upper distal center harness plate 1600, upper center harness plate ridge 1700, and scrotal opening 1800. When assembled the outer ridge of the sheath flange 1300 proximately abuts the harness plate including the harness plate distal side section 1100, harness plate distal upper region 1200. The perineum bump 900, outer perineum notch 1000, and inner perineum notch 1400 are located on the saddle region of the chassis 2600. When assembled, the saddles of the sheath 2500 and chassis 2600 align so that openings in their respective bases form the scrotal opening 1800. When orientated for use, the top of the devices are the respective sides opposite from the scrotal opening 1800 and saddle. Although it is often desired to have a scrotal opening, other variations including scrotal bags, saddle-less devices and those without perineum bumps are useful and within the scope of the inventions disclosed herein.

Figure 2:
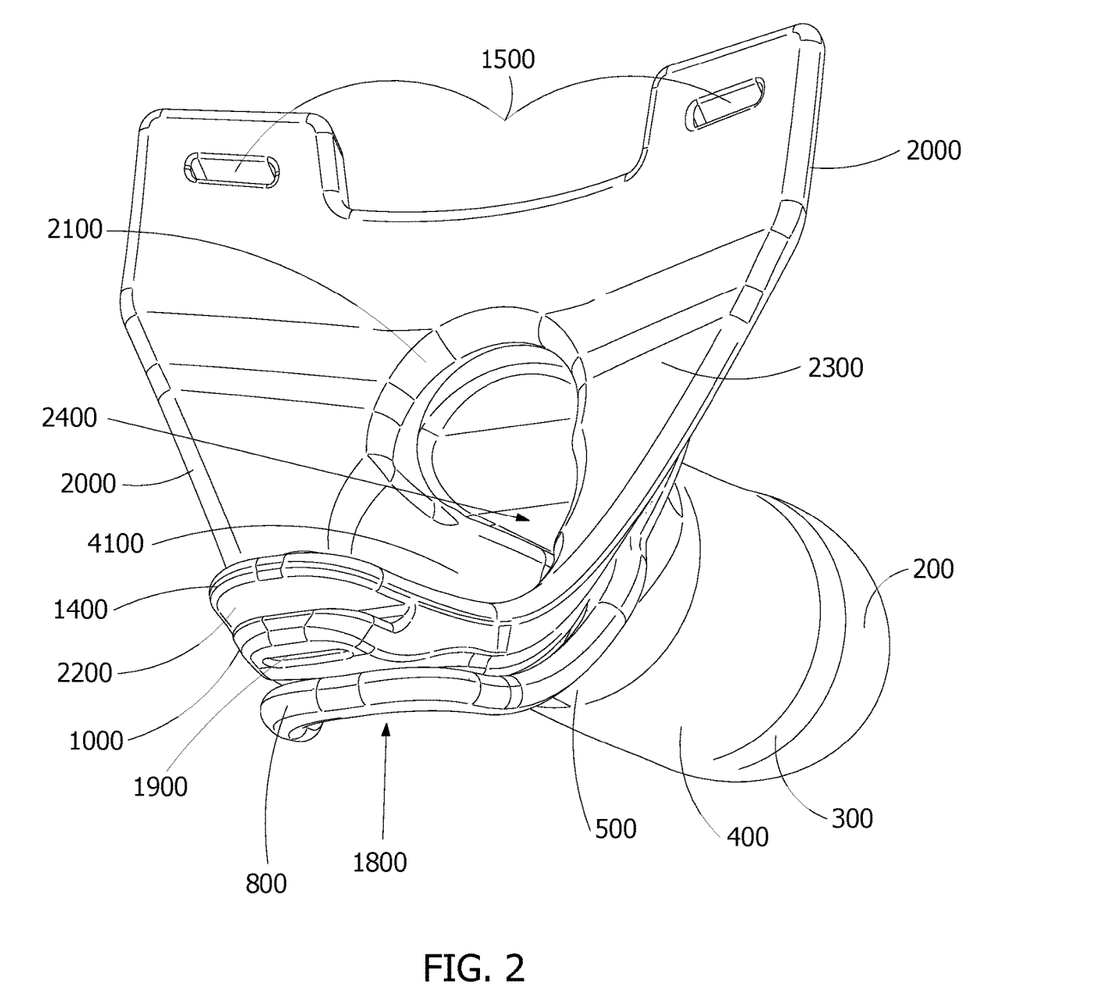
FIG. 2 is an elevated proximal view of the invention shown in FIG. 1.

FIG. 2. shows an elevated proximal view of the assembled sexual aid device and system. As drawn the sexual aid device and system comprise a perineum strap slot 1900, harness plate outer rim 2000, upper inner rim of harness plate of the penile port 2100, opening of the perineum notch 2200, harness plate proximal side section 2300, penile port 2400, and base lower chassis penile channel 4100. The harness plate strap slots 1500 and perineum strap slot 1900 can be replaced with other forms of connection to straps or a harness, including but not limited to snaps, buttons, clips, clamps, permeant fasteners, screws, bolts, ties, swivels, rivets, pins, etc.

FIG. 3. shows an exploded distal view of the invention shown in FIG. 1. FIG. 3. illustrates the separation of the sheath 2500 from the chassis 2600 to expose the base lower chassis penile support 4000.

Figure 4:
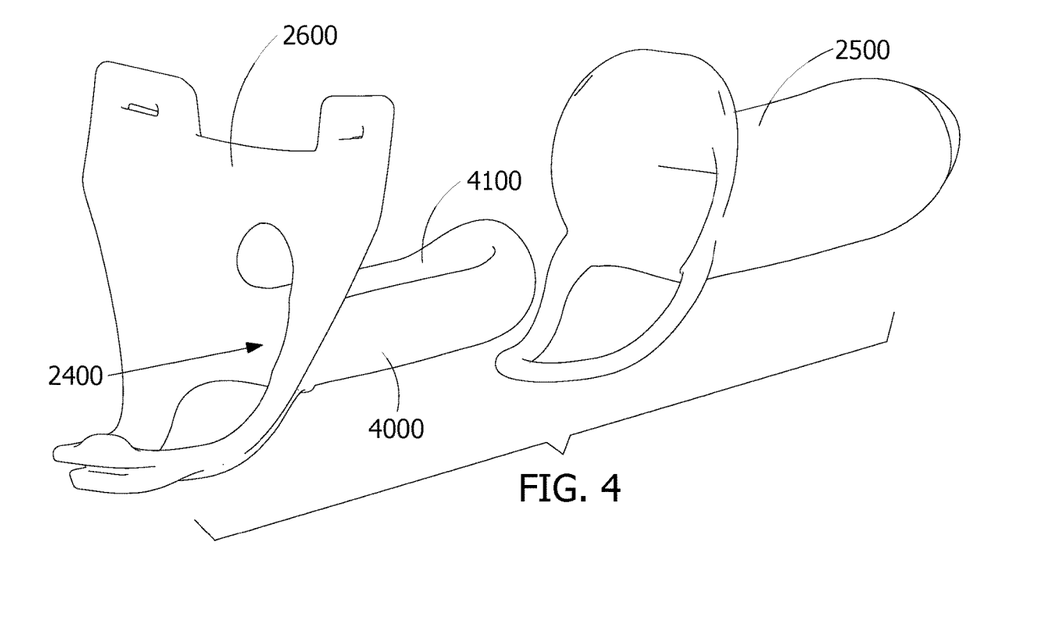
FIG. 4 is an exploded proximal view of the invention shown in FIG. 1.

FIG. 4. is an exploded proximal view of the invention shown in FIG. 1. FIG. 4. illustrates the separation of the sheath 2500 from the chassis 2600 to expose the base lower chassis penile support 4000. Also visible and identified by number are the base lower chassis penile channel 4100 and penile port 2400.

Figure 5:
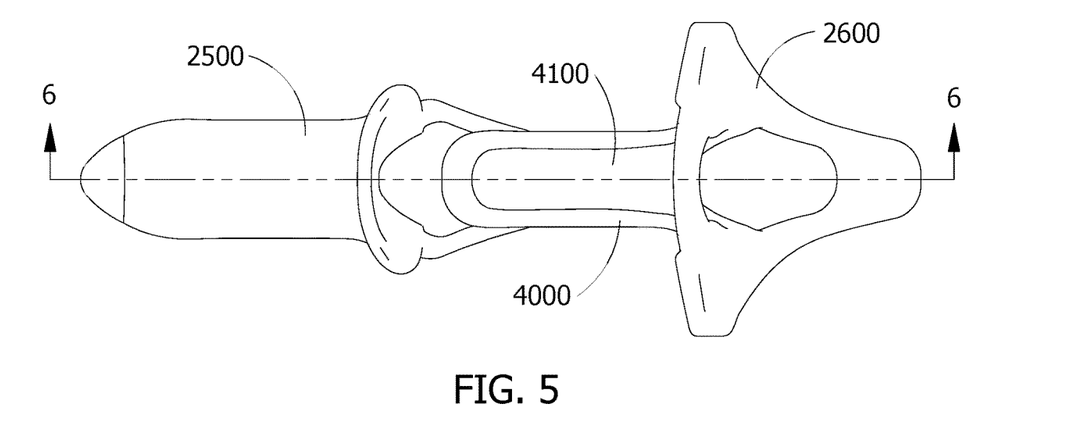
FIG. 5 is an exploded top down view of the invention shown in FIG. 1

FIG. 5 is an exploded top down view of the invention shown in FIG. 1. FIG. 5. illustrates the separation of the sheath 2500 from the chassis 2600 to expose the base lower chassis penile support 4000. Also, visible and identified by number are the base lower chassis penile channel 4100 and penile port 2400.

Figure 6:
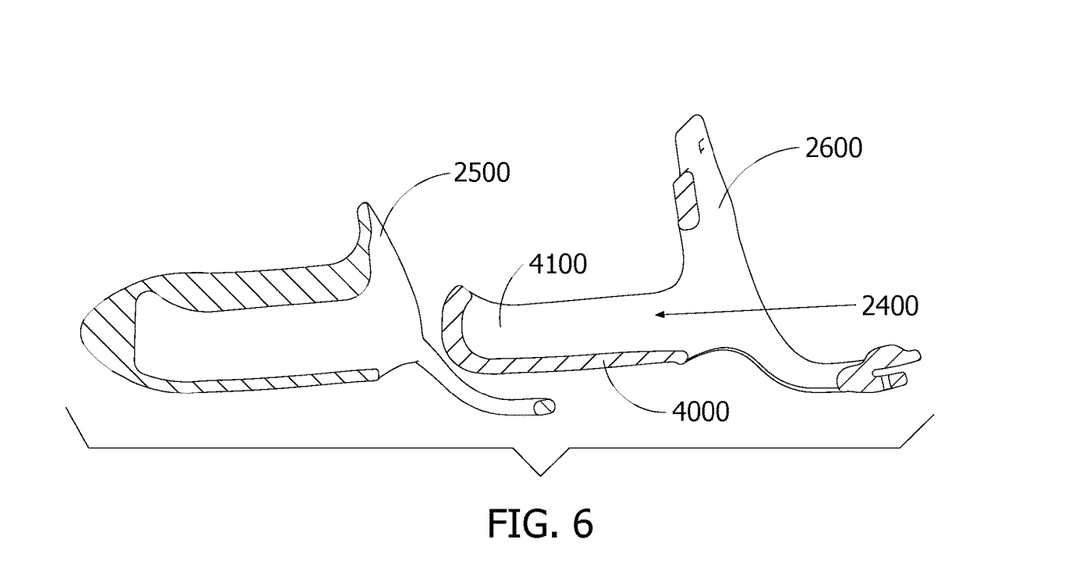
FIG. 6 is a cutaway side view of the FIG. 5 of the invention shown in FIG. 1.

FIG. 6 is a cutaway side view of the FIG. 5 of the invention shown in FIG. 1. FIG. 6. illustrates the separation of the sheath 2500 from the chassis 2600 to expose the base lower chassis penile support 4000. Also, visible and identified by number are the base lower chassis penile channel 4100 and penile port 2400.

Figure 7:
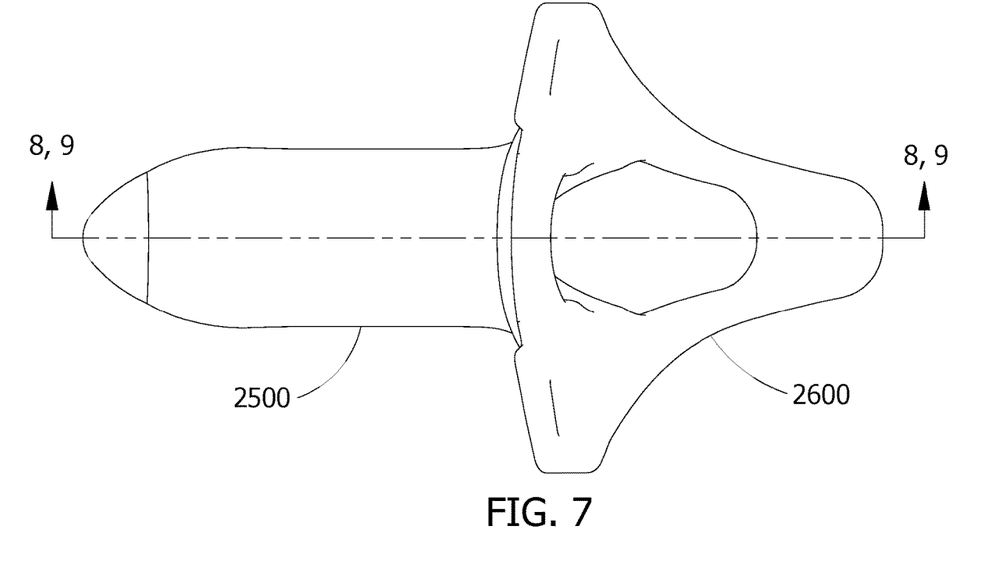
FIG. 7 is a top down view of the invention of FIG. 1.

FIG. 7 is a top down view of the invention of FIG. 1. FIG. 7. illustrates the joinder of the sheath 2500 and the chassis 2600.

Figure 8:
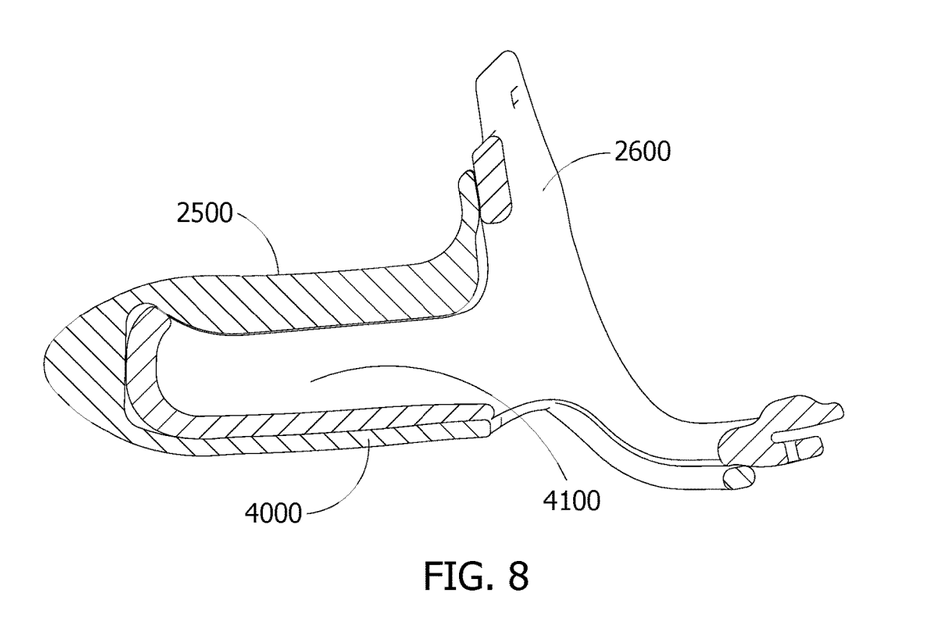
FIG. 8 is a cutaway side view of the invention of FIG. 1.

FIG. 8 is a cutaway side view of the invention of FIG. 1. FIG. 8. illustrates the joinder of the sheath 2500 and the chassis 2600. Also, visible and identified by number are the base lower chassis penile channel 4100 and penile support 4000.

Figure 9:
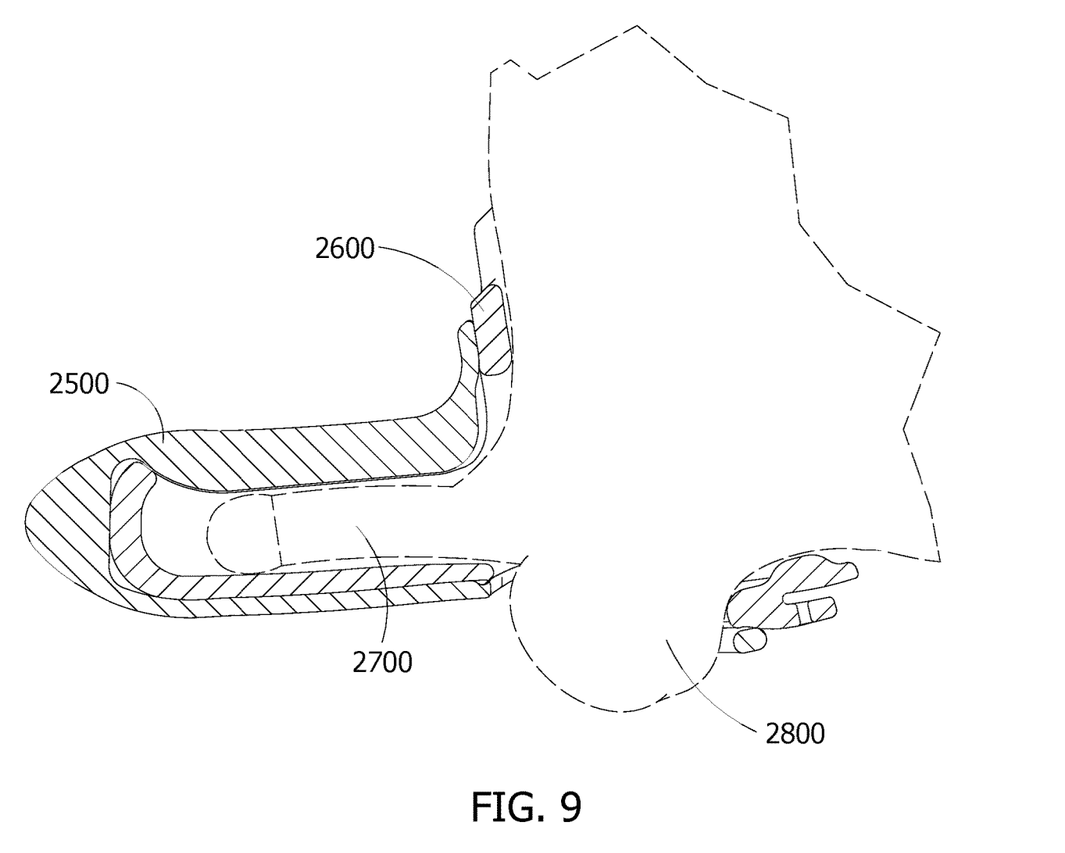
FIG. 9 is a cutaway side view of the invention of FIG. 1 as donned by a user.

FIG. 9 is a cutaway side view of the invention of FIG. 1 as donned by a user. Visible in FIG. 9 are the sheath 2500 and chassis 2600. A penis is inserted through the penile port 2400 into the penile channel 4100. The penile channel 4100 formed by the penile support 4000. The donning user's scrotum 2800 descends through the scrotal opening 1800.

Figure 10:
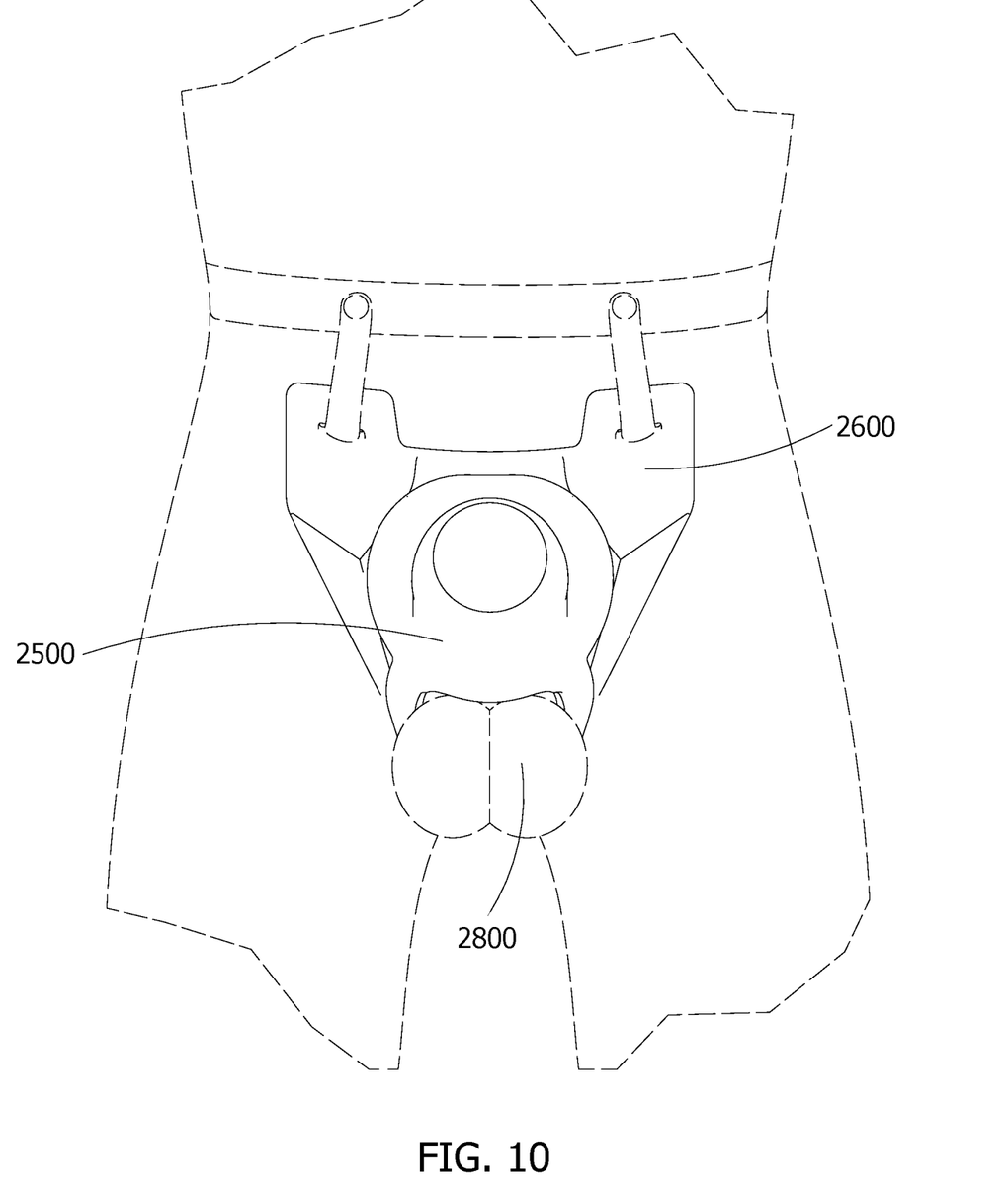
FIG. 10 is a distal view of the invention of FIG. 1 as donned by a user.

FIG. 10 is a distal view of the invention of FIG. 1 as donned by a user. Visible and identified by number are the sheath 2500, chassis 2600 and user scrotum 2800 descending through the scrotal opening 1800.

Figure 11:
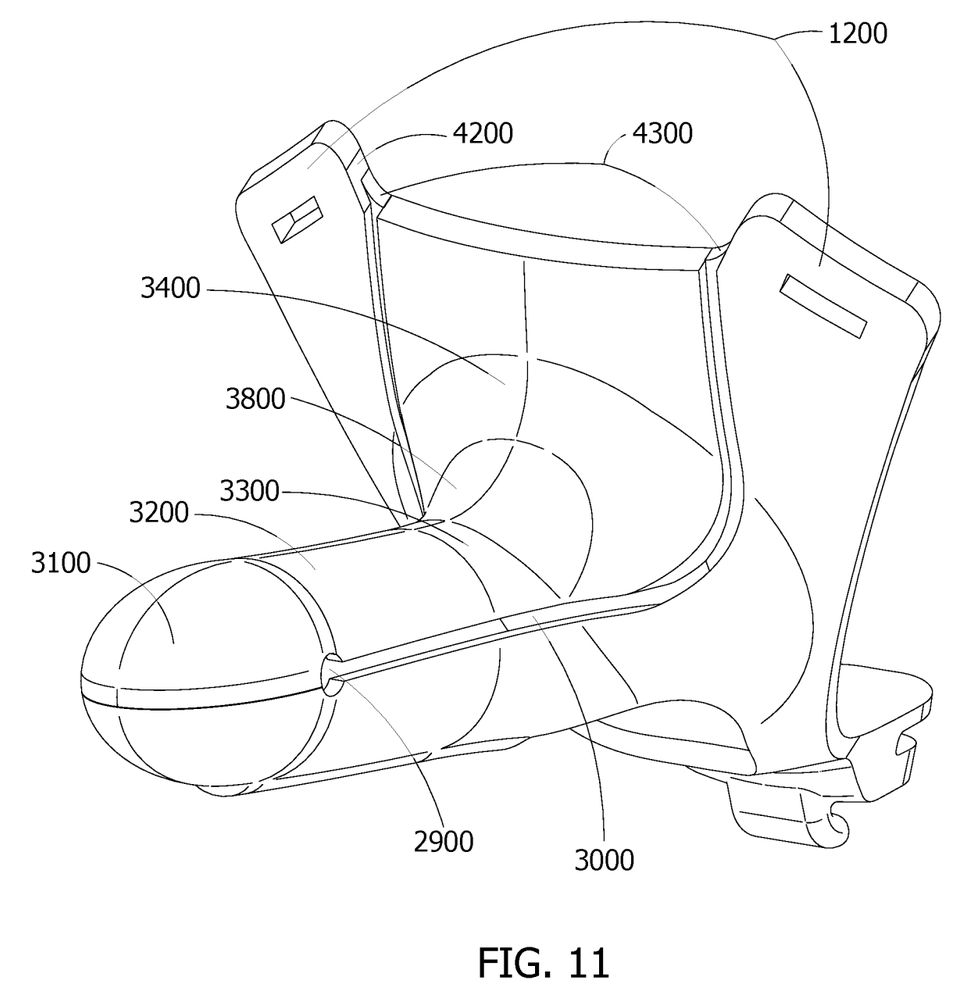
FIG. 11 is an elevated distal view of an alternative embodiment of the invention.

FIG. 11 is an elevated distal view of an alternative embodiment of the invention. As illustrated in FIG. 11, the alternative embodiment comprises: a hinge/pivot point/fulcrum 2900, a front upper chassis 3100, base upper chassis 3200, center upper chassis 3300, outer upper chassis central 3400, harness plate cutaway upper region 4200, upper chassis harness plate connector 4300, and harness plate distal upper region 1200.

Figure 12:
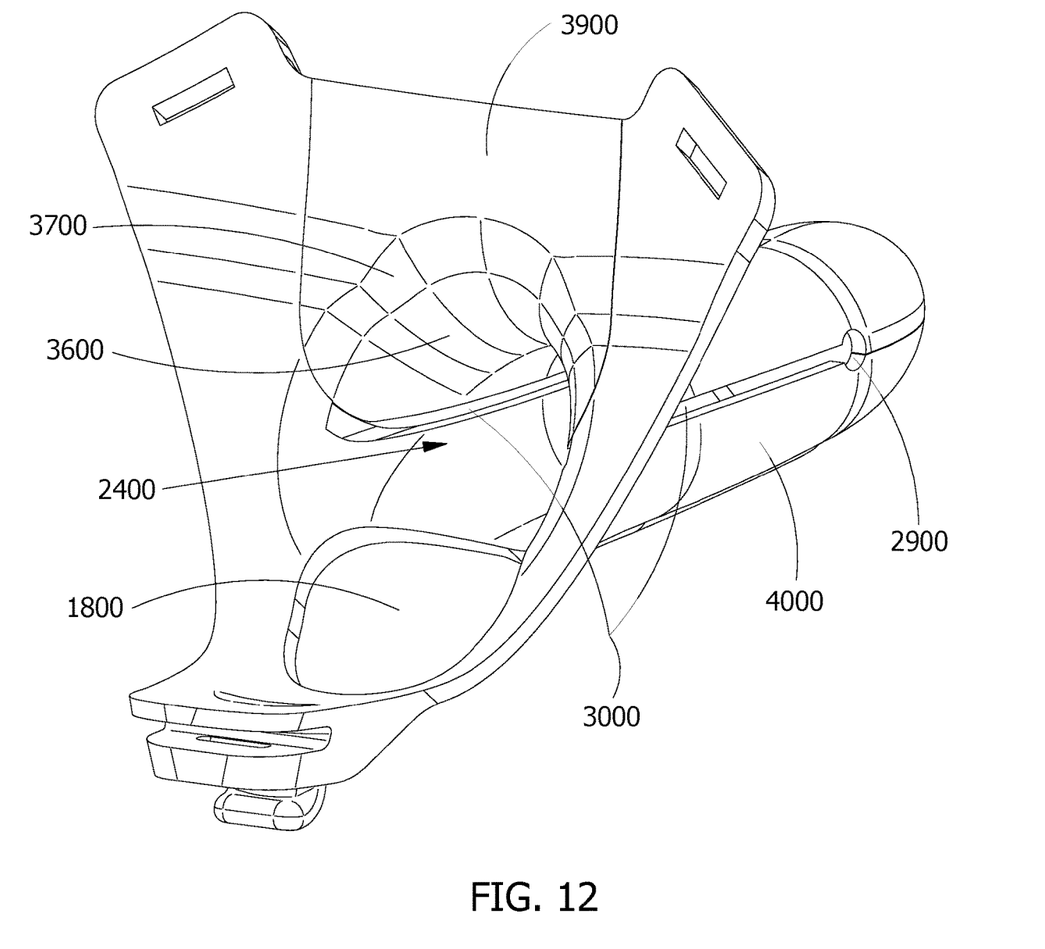
FIG. 12 is an elevated proximal of the invention of FIG. 11.

FIG. 12 further illustrates an elevated proximal of the invention of FIG. 11 showing a hinge/pivot point/fulcrum 2900, seam 3000, interior center upper chassis 3600, interior upper chassis transition 3700, interior upper chassis central harness plate 3900, and base lower chassis penile support 4000.

Figure 13:
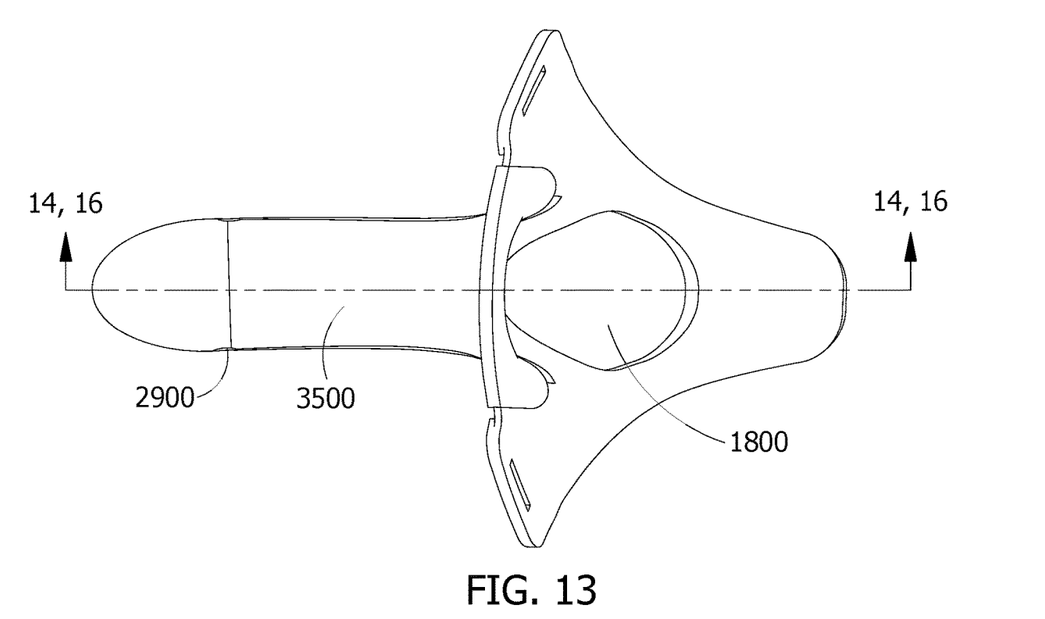
FIG. 13 is a top down view of the invention of FIG. 11.

FIG. 13 is a top down view of the invention of FIG. 11. FIG. 13. illustrates the hinge/pivot point/fulcrum 2900, upper chassis plate 3500 and scrotal opening 1800.

Figure 14:
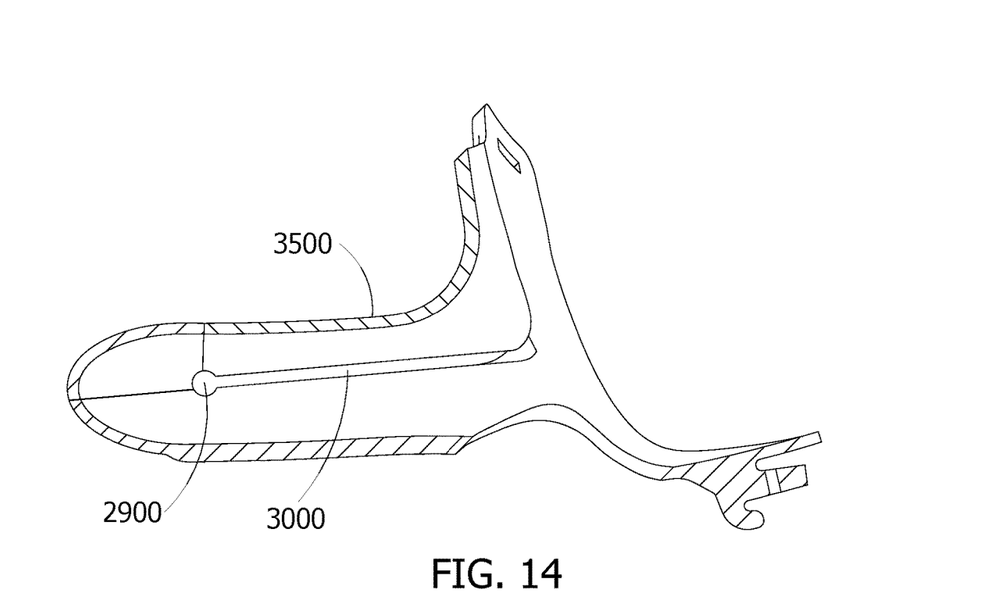
FIG. 14 is a cutaway side view of the invention of FIG. 11.

FIG. 14 is a cutaway side view of the invention of FIG. 11. FIG. 14. illustrates the hinge/pivot point/fulcrum 2900, upper chassis plate 3500 and seam 3000.

Figure 15:
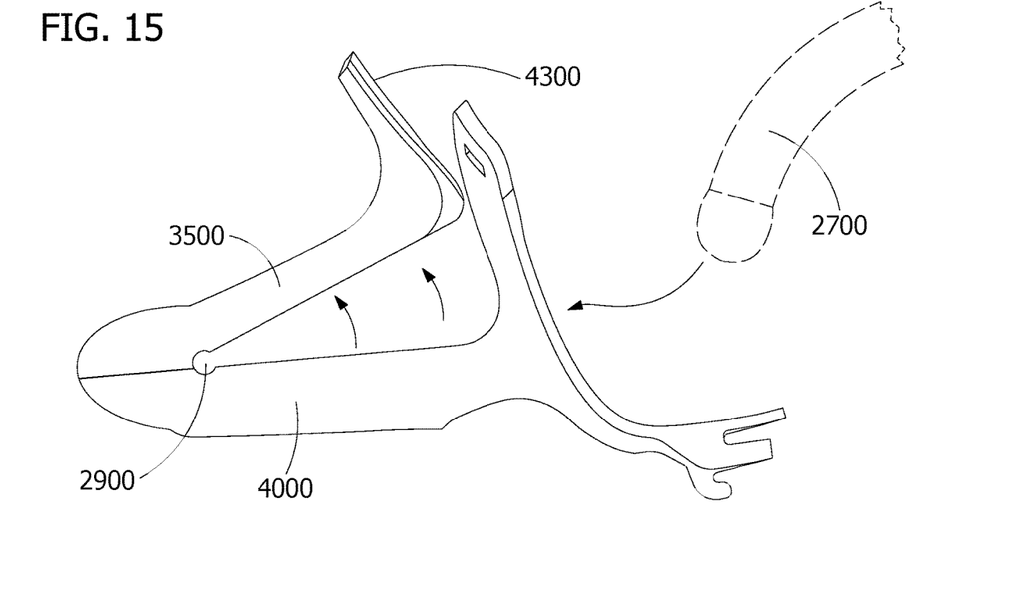
FIG. 15 is a side view of the invention of FIG. 11 wherein the upper chassis plate is in the open position.

FIG. 15 is a side view of the invention of FIG. 11 wherein the upper chassis plate 3500 is in the open position. Upper chassis harness plate connector 4300 is disconnected and upper chassis plate 3500 is opened by lifting the upper chassis plate 3500 away from the penile support 4000, which causes upper chassis plate to pivot on the hinge/pivot point/fulcrum 2900. Then, penis 2700 is inserted through the penile port 2400 and supported by the penile support 4000. As drawn the hinge/pivot point/fulcrum 2900 is orientated toward the distal end of the chassis 2600 so that when the upper chassis plate 3500 is in the open position there is an opening in the top of the chassis 2600 approximately toward the proximal end of the chassis 2600. Although it is not required that the opening actually open into the proximal end, having the opening extend through both the penile port 2400 and penile channel 4100 makes it easier to don the device. Although the hinge/pivot point/fulcrum 2900 is drawn toward the distal end of the chassis, a hinge/pivot point/fulcrum may also be placed at the proximal end or upon the side, along the seam. More than one hinge/pivot point/fulcrum may be used, and the upper chassis plate may open in multiple directions. For example, in some embodiments there is no hinge/pivot point/fulcrum and the upper chassis plate may slide open or be removable and attached by latches, snaps, clamps, compression fittings and other means to the penile support and/or other parts of the chassis 2600.

Figure 16:
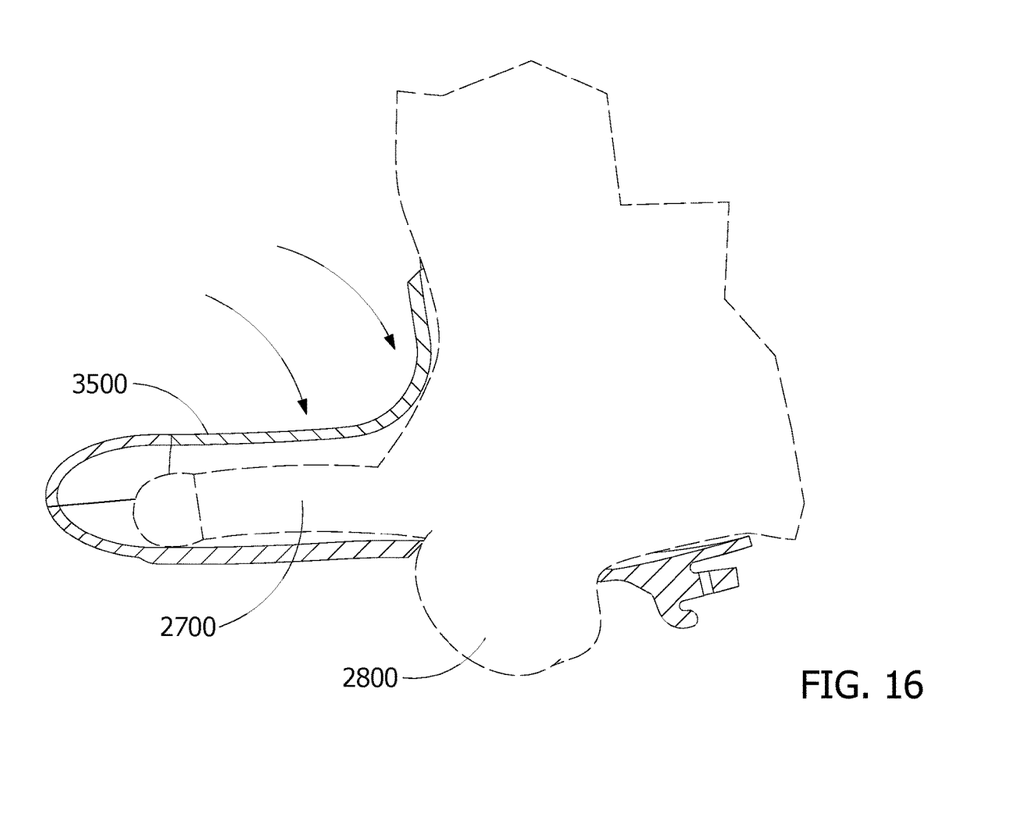
FIG. 16 is a cut away side view of the invention of FIG. 11 wherein the upper chassis plate in a closed position and the invention is donned by the user.

FIG. 16 is a cut away side view of the invention of FIG. 11 wherein the upper chassis plate 3500 in a closed position and the invention is donned by the user. Once a penis enters through the penile port 2400 into the penile channel 4100 and supported by the penile support 4000, the upper chassis plate 3500 is closed. The user's scrotum 2800 descends through the scrotal opening 1800.

The opening in the chassis toward the proximal end enables a donning user to easily and and comfortably rest/place a flaccid penis inside or on top of the device. The upper chassis plate and/or sheath provide fuller support for the flaccid penis so that when properly used the distal end of the device can penetrate a receiving user, while providing the donning user with support comfort and unique sexual stimulation. Having the device in the open positions enables the flaccid penis to have the sensation of flying through the breeze. Although the device can be used by persons with erectile dysfunction and/or suffering from premature ejaculation, it is also adapted to accommodate an erect penis so that a person with normal or increased sexual stamina and energy can use the device with an erect penis.

After climax, if the penis softens or becomes less erect, the donning user can continue to pleasure their sexual partner. This is an encore method of intercourse. The sexual aid device may be utilized before or after climax. The opening in the top of the chassis that forms the penile channel 4100 enables the device when opened to be easily donned by a person with a flaccid penis as it does not require an erect penis inserted through the penile port, but allows the penis 2700 to be dropped in from the top, see e.g. FIG. 15. This advantage is realized in both the hard top embodiments drawn in FIGS. 11-16, and the soft-top and open top embodiments shown in FIGS. 1-10.

In a preferred embodiment, the chassis of sexual aid device and system of the present invention is made of a single material from a single mold. The material used for a sexual aid device and system of the present invention may be nearly any solid material. However, a material used often has elastic properties in order to absorb energy and stretch to fit. In a preferred embodiment a sexual aid device and system of the present invention fits around a penis and is held in place by the testicles. This preferred embodiment provides an added benefit of enabling the automatic massaging, squeezing and pulling sensation around the testicles and/or perineum during intercourse that provides pleasure to the penetrating partner donning the device, similar to that of a reach around. For the penetrated/receiving partner that would normally provide a reach around, the device enables the penetrated partner to use their hands for other purposes, or for more specific stimulation of the penetrating partner's testicles and perineum which although automatically stimulated are still accessible to the penetrated partner.

A preferred material for forming the chassis 2600 of the sexual aid device and system of the present invention contains polysiloxanes, a silicone plastic and/or silicone rubber blend. Various elastomers may also be used, including but not limited to natural rubbers. Ideally, in many cases, an inert or medical grade silicone rubber, latex or silicone blended material is used. The recommended materials for forming a thrust bumper are biocompatible and hypoallergenic, but can also be treated with an antibiotic or antiviral coating and/or texture. Antibiotic material and/or chemicals may also be infused or formed within the material of the sexual aid device and system of the present invention. Springs, foams, padding, goose down, cotton, rayon, polyester, various microfibers and other materials such as memory foam may be used to form the sexual aid device and/or portions of its core. The chassis may use metals and other more rigid materials for structural support. However, it is desirable that the outer and inner surfaces are soft and hygienic.

The sexual aid device and system of the present invention core may contain gels, liquids and/or other materials. However, too much memory or too much elasticity of the material that comprise a sexual aid device and system of the present invention may adversely effect the results. Moreover, many springs, foams, padding and other materials often lack the generally desired hypoallergenic characteristics. The best materials generally are: highly elastic; quickly to return to their stable (molded or cut) form; resist/prevent and/or destroy bacteria, fungus and viruses; and, are easily washed. A preferred embodiment of a chassis of the present invention compresses during thrusting of sexual intercourse and expands during withdraw. Generally, the material forming a sexual aid device and system of the present invention should feel comfortable to the touch and soft, silky, and skin like. However, some users desire a more rigid, leathery, wet or rough feel. Ribbing, various textures such as surface spikes and treats are applied to some devices for additional sensation, pleasure and comfort.

The internal edges and outer edges of the sheath 2500 and chassis 2600 are preferably smooth and beveled/rounded. Preferably, the edges are eased, but bullnose, ogee, straight and other forms of edge may be used. The rounded edges generally provide greater comfort and make it easier for a user to don the sexual aid device and prevent chaffing.

Often the materials for forming the sheath 2500 of the sexual aid device and system of the present invention are those containing polysiloxanes, a silicone plastic and/or silicone rubber blend. Various elastomers may also be used, including but not limited to natural rubbers. Ideally, in many cases, an inert or medical grade silicone rubber, latex or silicone blended material is used. The recommended materials for forming the sheath are biocompatible and hypoallergenic, but can also be treated with an antibiotic or antiviral coating and/or texture. Antibiotic material and/or chemicals may also be infused or formed within the material of the sexual aid device and system of the present invention. Thin and disposable sheaths are desirable in many instances and materials such as lambskin or condoms are used. Spermicidal, antibiotic, lubricants, warming gels, cooling gels and antiviral coatings can enhance the sexual experience and prophylactic use of the device. Various textures, ribbing and treads patterns can be applied to the inner and outer surfaces of the sheath for greater sensation and control by both the donning user and the receiving person.

Beveling and grooving/texturing of the exterior edges also provides a comfortable fit while enabling better grip for donning and removing the device. Examples of various embodiments of external edges and groves are shown in the figures.

In order to don a sexual aid device, the giving and/or penetrating partner places his/her penis/phallus and/or appendage through the opening in the top of the device. When using with a sheath 2500 the sheath 2500 should be removed prior to placement of the penis. However, if erect the device may be donned by direct insertion of the penis 2700 through the penile port 2400. In a preferred embodiment the penetrating partner also inserts his testicles so that the testicles and scrotum 2800 descend through the scrotal opening 1800. The scrotal opening 1800 chassis inner edge, scrotal port chassis inner wall, sheath inner scrotal support 700 and sheath outer scrotal support 800 surround the scrotal opening 1800. The scrotal opening 1800 and the surrounding saddle(s) enable hands free use, stability and stimulation of the scrotum 2800 and testicles during intercourse.

In some embodiments the penile port 2400 and/or scrotal opening 1800 are narrowed in order to provide erection ring type support for longer sex and greater engorgement of the penis. This is particularly useful when the donning/penetrating partner desires the sensation of an erection but suffers from erectile dysfunction, premature ejaculation, and/or is recovering from prior climax.

While results vary slightly across reputable studies, the general consensus is that the mean human penis, when erect, is in the range 12.9-15 cm (5.1-5.9 in) in length. The average girth is about four and fifty nine one-hundredths (4.59) inches in circumference. Consequently, the desired length of the penile channel from the proximal end of the penile port 2400 to the distal end should generally be greater than six (6) inches. In most applications, seven (7) inches or more is desired. The penile port 2400 circumference generally should be at least approximately one and one-half (1.5) inches and generally less than seven (7) inches. In most applications, between four (4) to six (6) inches of circumference is desired. The most common width being approximately one and one-half (1.5) inches or just under five (5) inches in circumference. However, some penile channel 4100 and penile port 2400 shapes and size may exceed or fall outside the generally recommended rages. In particular, in some applications it is desired to contain a vibrating mechanism(s), such as a unbalanced motor(s), spring(s) or bells. In these embodiments that chassis are often extended to include such mechanisms, and such mechanisms are activated prior and/or during insertion of the sexual aid device into an orifice. The drawings herein are understood to be just representative embodiments, other embodiments and combinations are also described herein.

Having thus described preferred embodiments, it should be apparent to those skilled in the art that certain advantages of the described system have been achieved. It should also be appreciated that various modifications, adaptions, and alternative embodiments thereof may be made within the scope and spirit of the present invention. The invention is further defined by the following claims.

What is claimed is:
1. A sexual aid device comprising:
   a chassis comprising:
      a top;
      a bottom;
      a distal end;

an upper chassis plate;
a proximal end with at least one penile port;
at least one penile support between the distal end and proximal end; and,
at least one penile channel between the distal end and proximal end;
wherein the chassis is configured to have an opening along the top approximately toward at least the proximal end; and,
wherein the upper chassis plate is secured in a closed position by a connector on a harness plate formed of part of the proximal end of the chassis.

2. The sexual aid device of claim 1, further comprising: a scrotal opening.

3. A sexual aid device of claim 2, further comprising:
a sheath comprising:
a sheath outer distal center tip;
a sheath outer distal outer tip;
a sheath outer distal shaft;
sheath outer center shaft; and,
a sheath outer proximal shaft.

4. A sexual aid device of claim 3, further comprising:
a sheath outer flange.

5. A sexual aid device of claim 4, further comprising:
a sheath inner scrotal support; and,
a sheath outer scrotal support.

6. A sexual aid device of claim 1, further comprising:
a hinge/pivot point/fulcrum.

7. A sexual aid device of claim 6, further comprising:
a front upper chassis
base upper chassis
center upper chassis.

8. A sexual aid device of claim 7, further comprising:
outer upper chassis central harness plate
upper chassis harness plate connector, and
harness plate distal upper region.

9. A sexual aid device of claim 8, wherein hinge/pivot point/fulcrum is located on the top of the chassis toward the distal end so that when opened the upper chassis plate opens away from the donning user to exposing the opening along the top approximately toward at least the proximal end.

10. A method of sexual intercourse comprising:
donning with a flaccid penis:
a sexual aid device comprising:
a chassis comprising:
a top;
a bottom;
a distal end;
a proximal end with at least one penile port;
at least one penile support between the distal end and proximal end; and,
at least one penile channel between the distal end and proximal end;
wherein the chassis is configured to have an opening along the top approximately toward at least the proximal end;
wherein prior to insertion into the orifice an upper chassis plate covers in whole or in part the top of the chassis;
wherein the upper chassis plate is secured in a closed position prior into insertion into the orifice by a connector on a harness plate formed of part of the proximal end of the chassis; and,
inserting the sexual aid device into an orifice.

11. The method of claim 10 wherein the penis is flaccid when the sexual aid device is inserted into the orifice.

12. The method claim 11 wherein prior to inserting the sexual aid device into the orifice a sheath is pulled over the chassis.

13. The method of claim 11 wherein a scrotal opening in the chassis is adopted to enable descent of the scrotum of the donning user.

14. The method of claim 11 wherein a scrotal opening in the sheath is adopted to enable descent of the scrotum of the donning user.

15. The method of claim 11 wherein the upper chassis plate pivots along an upper portion of the chassis body.

16. A system of sexual aid devices used for sexual intercourse comprising:
a chassis comprising an upper chassis plate; and,
a sheath;
wherein the chassis provides one or more penile supports adopted to support a penis;
wherein the upper chassis plate is secured in a closed position by a connector on a harness plate formed of part of the proximal end of the chassis;
and, the sheath covers the portions of the penile support adopted for insertion into an orifice.

17. The system of claim 16 wherein the system further comprises:
a scrotal opening formed by:
a chassis inner edge;
scrotal port chassis inner wall;
sheath inner scrotal support;
sheath outer scrotal support surrounding the scrotal opening; and,
a surrounding saddle adopted to extend into the perineum of a donning user.

* * * * *